(12) United States Patent
Ozawa

(10) Patent No.: US 11,383,045 B2
(45) Date of Patent: Jul. 12, 2022

(54) INJECTOR GASKET FALLING-OFF PREVENTION MECHANISM

(71) Applicant: Maeda Industry Co., Ltd., Osaka (JP)

(72) Inventor: Kazuhiro Ozawa, Osaka (JP)

(73) Assignee: Maeda Industry Co., Ltd., Osaka (JP)

( * ) Notice: Subject to any disclaimer, the term of this patent is extended or adjusted under 35 U.S.C. 154(b) by 306 days.

(21) Appl. No.: 16/651,582

(22) PCT Filed: Oct. 18, 2017

(86) PCT No.: PCT/JP2017/037738
§ 371 (c)(1),
(2) Date: Mar. 27, 2020

(87) PCT Pub. No.: WO2019/077703
PCT Pub. Date: Apr. 25, 2019

(65) Prior Publication Data
US 2020/0254184 A1    Aug. 13, 2020

(51) Int. Cl.
*A61M 5/315*      (2006.01)

(52) U.S. Cl.
CPC .... *A61M 5/31566* (2013.01); *A61M 5/31501* (2013.01); *A61M 5/31513* (2013.01);
(Continued)

(58) Field of Classification Search
CPC .......... A61M 5/31566; A61M 5/31501; A61M 5/31513; A61M 5/31515; A61M 5/31535;
(Continued)

(56) References Cited

U.S. PATENT DOCUMENTS 5,607,399 A    3/1997  Grimard et al.
9,770,559 B2 *  9/2017  Armstrong .......... A61M 5/3134
(Continued)

FOREIGN PATENT DOCUMENTS

EP    2 298 392 A1    3/2011
JP    2001-327600 A   11/2001
(Continued)

OTHER PUBLICATIONS

Extended European Search Report issued in European Application No. 17929221.4 dated Apr. 26, 2021 (seven (7) pages).
(Continued)

*Primary Examiner* — Brandy S Lee
*Assistant Examiner* — Hong-Van N Trinh
(74) *Attorney, Agent, or Firm* — Crowell & Moring LLP

(57) ABSTRACT

A stopper being adapted to be fixed in a rear end portion of a syringe is provided. The stopper is reduced in diameter at a fitting portion of a rod portion of a plunger rod so as to have a diameter smaller than an inner diameter of the rear end portion and be insertable into the rear end portion. After insertion, the stopper is increased in diameter and is fixed in the rear end portion so as not to be movable in an axial direction by fitting a first recessed portion on a periphery into a second protruding portion of an inner surface of the rear end portion. The stopper has, on an inner surface, a third protruding portion having an inner diameter smaller than an outer diameter of a gasket support flange of the rod portion in a fixed state.

6 Claims, 15 Drawing Sheets

(52) U.S. Cl.
CPC .... *A61M 5/31515* (2013.01); *A61M 5/31535* (2013.01); *A61M 2005/31508* (2013.01)

(58) Field of Classification Search
CPC .... A61M 2005/31508; A61M 5/31505; A61M 2005/3151; A61M 2005/31506
See application file for complete search history.

(56) References Cited

U.S. PATENT DOCUMENTS

| | | |
|---|---|---|
| 2004/0087907 A1 | 5/2004 | Smith et al. |
| 2008/0281266 A1 | 11/2008 | Walton et al. |
| 2016/0271340 A1 | 9/2016 | Walsh |
| 2018/0200448 A1* | 7/2018 | Caclin .............. A61M 5/31501 |

FOREIGN PATENT DOCUMENTS

| | | |
|---|---|---|
| JP | 2004-8639 A | 1/2004 |
| JP | 2004-65272 A | 3/2004 |
| JP | 2005-118238 A | 5/2005 |
| JP | 2008-253812 A | 10/2008 |
| JP | 2009-515609 A | 4/2009 |
| WO | WO 2017/005914 A1 | 1/2017 |
| WO | WO 2017/170635 A1 | 10/2017 |

OTHER PUBLICATIONS

International Search Report (PCT/ISA/210) issued in PCT Application No. PCT/JP2017/037738 dated Jan. 23, 2018 with English translation (four (4) pages).
Japanese-language Written Opinion (PCT/ISA/237) issued in PCT Application No. PCT/JP2017/037738 dated Jan. 23, 2018 (three (3) pages).

* cited by examiner

FRONT ⟷ REAR

INJECTOR GASKET FALLING-OFF PREVENTION MECHANISM

TECHNICAL FIELD

The present invention relates to a gasket falling-off prevention mechanism for preventing a gasket provided at the tip of a piston from falling off through a rear end opening of a syringe of an injector.

BACKGROUND ART

An injector in which a piston is inserted into a syringe is desirably excellent in airtightness and liquid tightness at the time of shipment, sterilization, and use. For this purpose, it is desirable that the gasket provided at the tip of the piston do not easily fall off from the syringe. It is particularly required to prevent the piston from being accidentally pulled out from the syringe during suction of a chemical liquid. Various structures for achieving this requirement, i.e., various gasket falling-off prevention mechanisms have been proposed so far.

PRIOR ART DOCUMENTS

Patent Documents

Patent Document 1: Japanese Patent Laid-open Publication No. 2008-253812
Patent Document 2: Japanese Patent Laid-open Publication No. 2005-118238
Patent Document 3: Japanese Patent Laid-open Publication No. 2004-65272
Patent Document 4: Japanese Patent Laid-open Publication No. 2004-8639
Patent Document 5: Japanese Patent Laid-open Publication No. 2001-327600
Patent Document 6: Japanese Translation of PCT International Application Publication No. 2009-515609

SUMMARY OF THE INVENTION

Problems to be Solved by the Invention

However, in many cases, conventional gasket falling-off prevention mechanisms have a complicated structure or poor productivity. In addition, in a conventional example where a falling-off prevention protruding portion is provided on an inner surface of a rear end portion of a syringe, there is a problem that a surface of a gasket is damaged due to the protruding portion when the gasket is inserted into the syringe.

An object of the present invention is to provide a gasket falling-off prevention mechanism capable of preventing a gasket from falling off with a simple structure.

Means for Solving the Problems

The present invention is a gasket falling-off prevention mechanism that is provided in an injector and prevents a gasket provided at the tip of a plunger from falling off through a rear end opening of a syringe, including a stopper being adapted to be fixed in a rear end portion of the syringe, in which: the stopper is a cylindrical body having a split groove, is externally fitted onto a small diameter portion of a rod of the plunger before fixing, is deformed in a direction of closing the split groove at the small diameter portion at the time of fixing so as to have a diameter smaller than an inner diameter of the rear end portion of the syringe and be insertable into the rear end portion, and, after insertion, is increased in diameter and is fixed in the rear end portion so as not to be movable in an axial direction by fitting a recessed portion on a periphery into a first protruding portion on an inner surface of the rear end portion of the syringe; and the stopper in a fixed state has a second protruding portion having an inner diameter smaller than an outer diameter of the gasket support flange of the rod.

Effects of the Invention

According to the present invention, by reducing a stopper in diameter at a small diameter portion of a rod, the stopper can be inserted into a rear end portion of a syringe and can further be fixed in the rear end portion so as not to be movable in an axial direction. In addition, the fixed stopper can prevent a gasket from falling off from the syringe. Thus, it is possible to achieve gasket falling-off prevention with a simple structure.

EMBODIMENTS OF THE INVENTION

Figure 1:
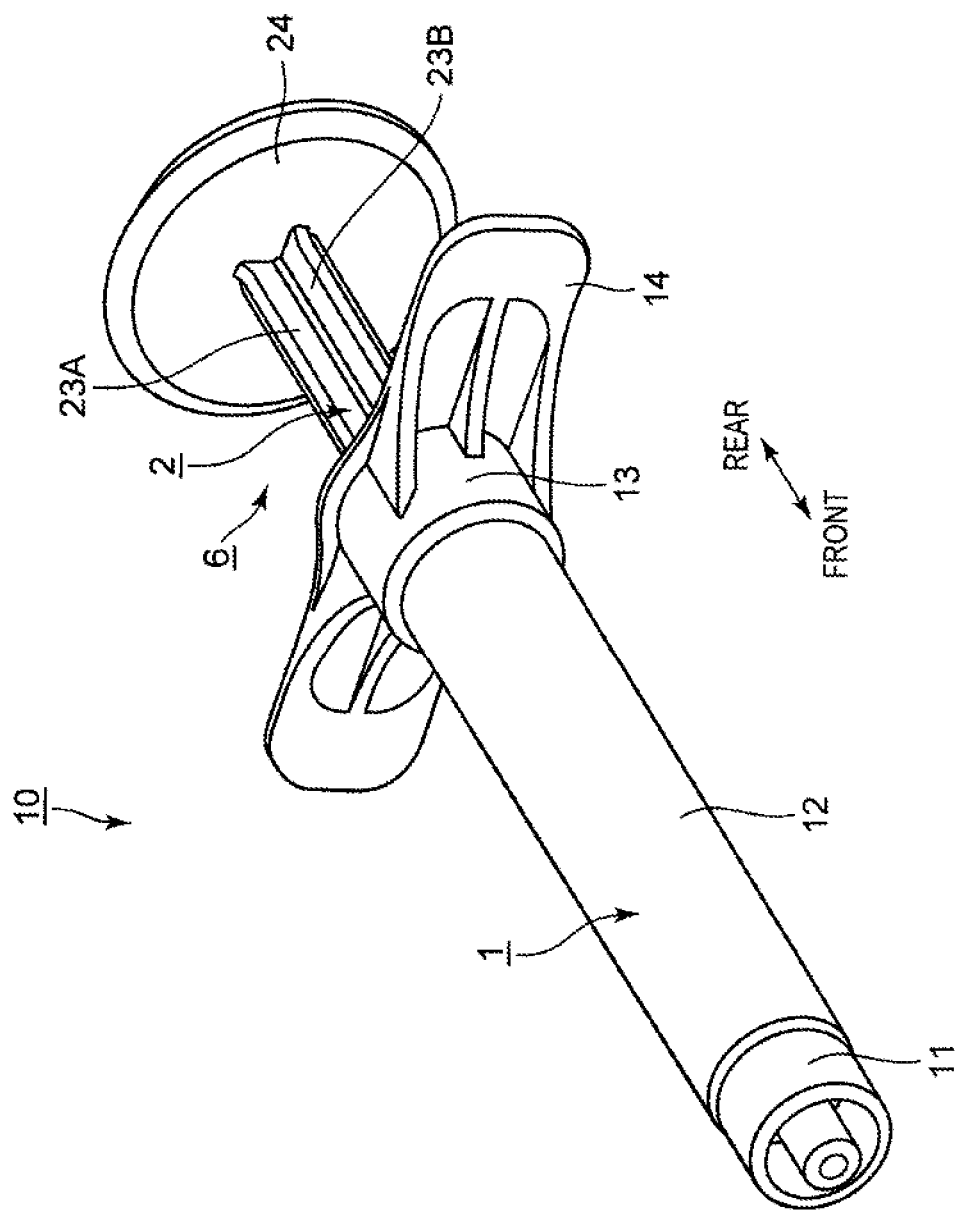
FIG. 1 is a front perspective view of an injector including a gasket falling-off prevention mechanism of the present invention.
Figure 2:
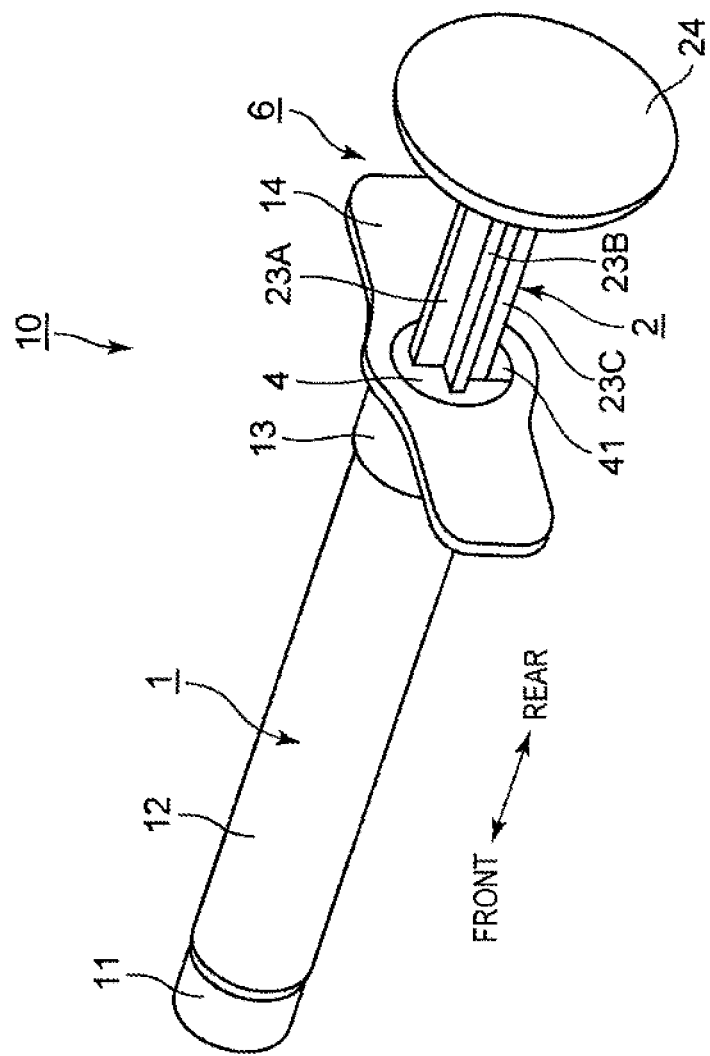
FIG. 2 is a rear perspective view of an injector.
Figure 3:
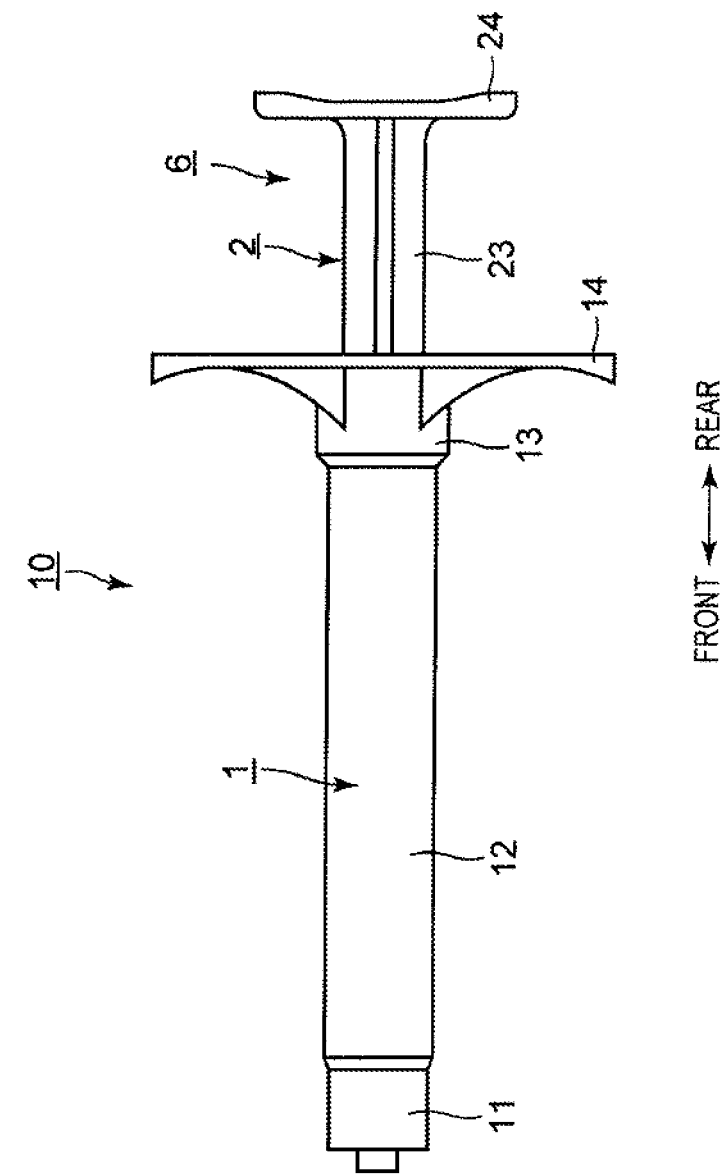
FIG. 3 is a plan view of an injector.
Figure 4:
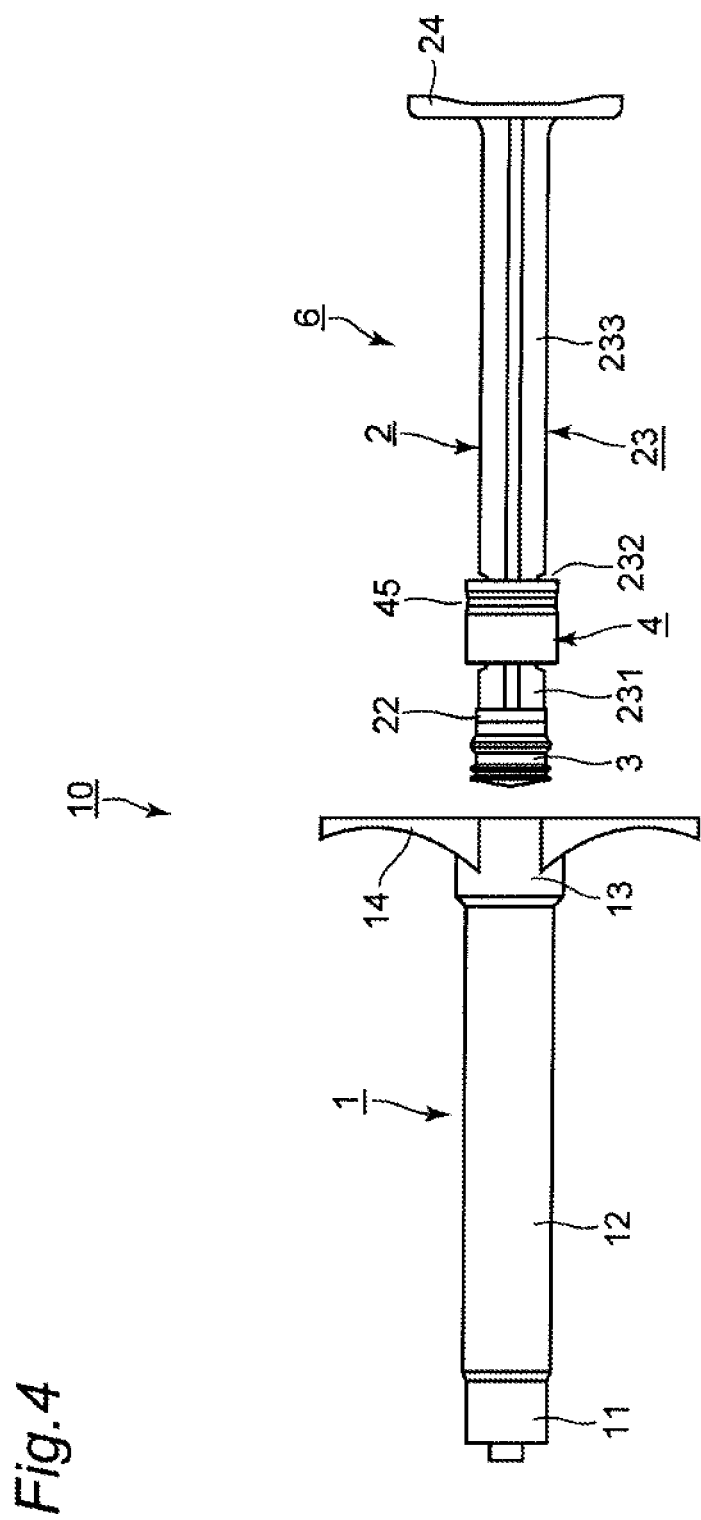
FIG. 4 is an exploded view of an injector.
Figure 5:
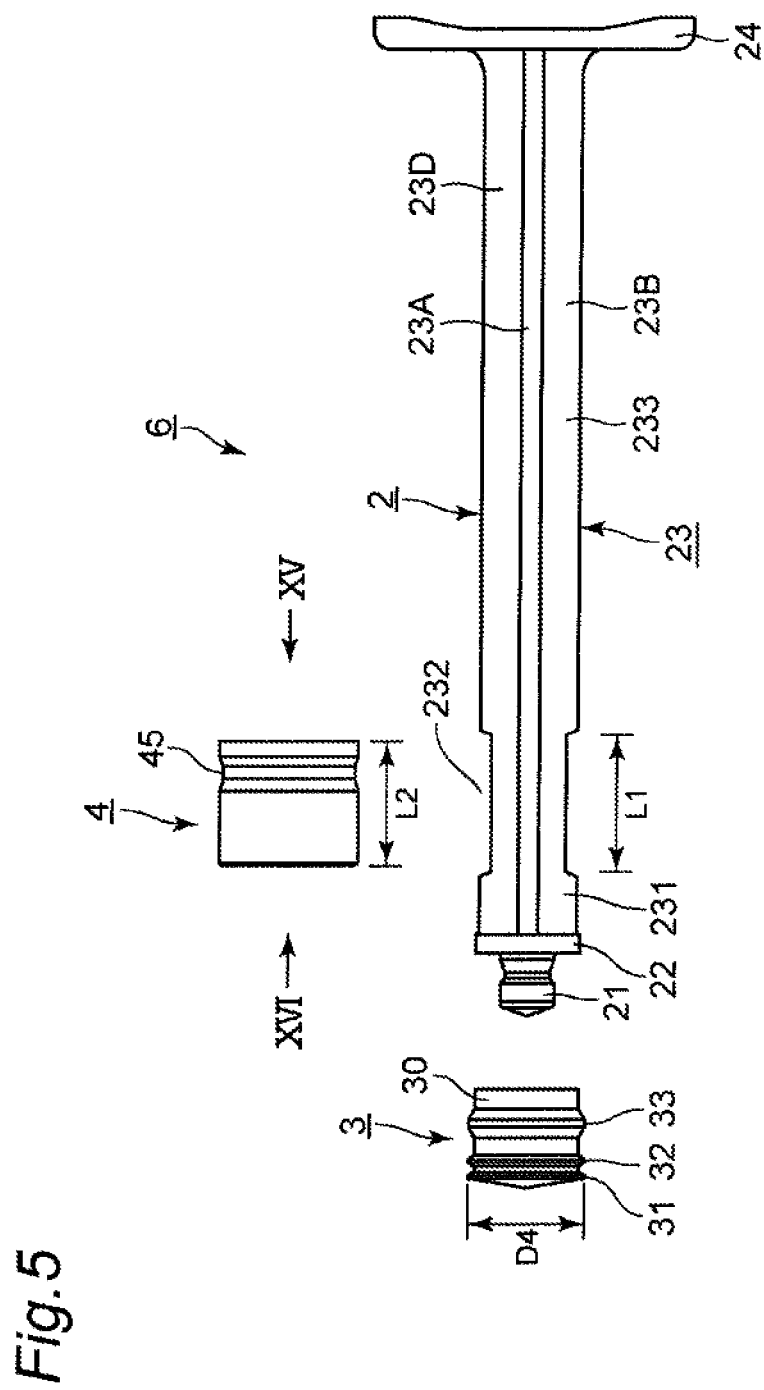
FIG. 5 is an exploded view of a piston.

FIG. 1 is a front perspective view of an injector 10 including a gasket falling-off prevention mechanism of the present invention. FIG. 2 is a rear perspective view of the injector 10. FIG. 3 is a plan view of the injector 10 of FIG. 1. The injector 10 includes a syringe 1 and a piston 6 inserted into the syringe 1. FIG. 4 is an exploded view of the injector 10. FIG. 5 is an exploded view of a plunger 2. A piston 6 includes the plunger rod 2 and a gasket 3 fixed to a tip thereof. The injector 10 further includes a gasket falling-off prevention mechanism. The gasket falling-off prevention mechanism includes a stopper 4. Note that illustration of an injection needle is omitted in the drawings.

Figure 6:
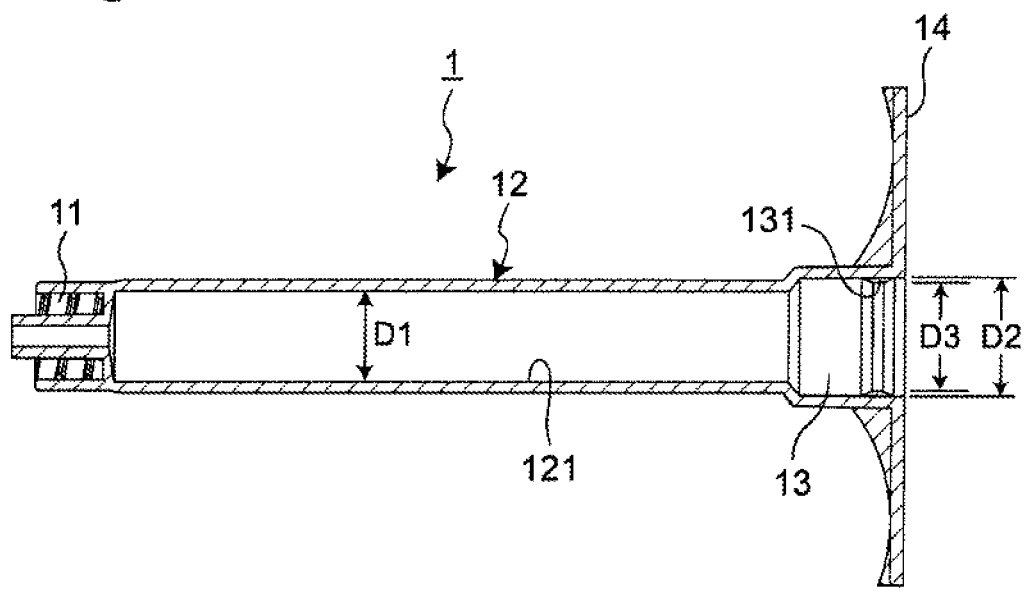
FIG. 6 is a cross-sectional plan view of a syringe.

FIG. 6 is a cross-sectional plan view of the syringe 1. The syringe 1 has a luer portion 11 to which the injection needle is attached, a main body 12 to be filled with an injection solution, a rear end portion 13 to which the stopper 4 is fixed, and a finger contact flange 14. An inner diameter D1 of the main body 12 may be gradually increased from a front end thereof to a rear end thereof or may be substantially the same. In the former case, it is easy to perform die cutting at the time of manufacture. The rear end portion 13 has an inner diameter D2 larger than the inner diameter D1 of the main body 12, and has a protruding portion (second protruding portion) 131 on an inner surface thereof. The protruding portion 131 is continuous in a circumferential direction. An inner diameter D3 of the protruding portion 131 is set to be the same as or slightly larger than an outer diameter D4 (FIG. 5) of the gasket 3.

The syringe 1 is preferably made from polypropylene resin, cycloolefin polymer resin, or cycloolefin copolymer resin.

Figure 7:
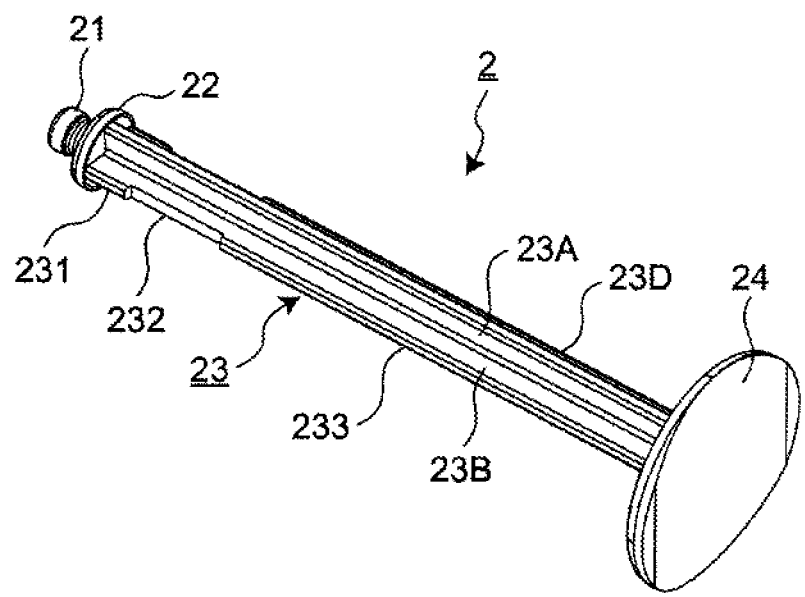
FIG. 7 is a rear perspective view of a plunger rod.
Figure 8:
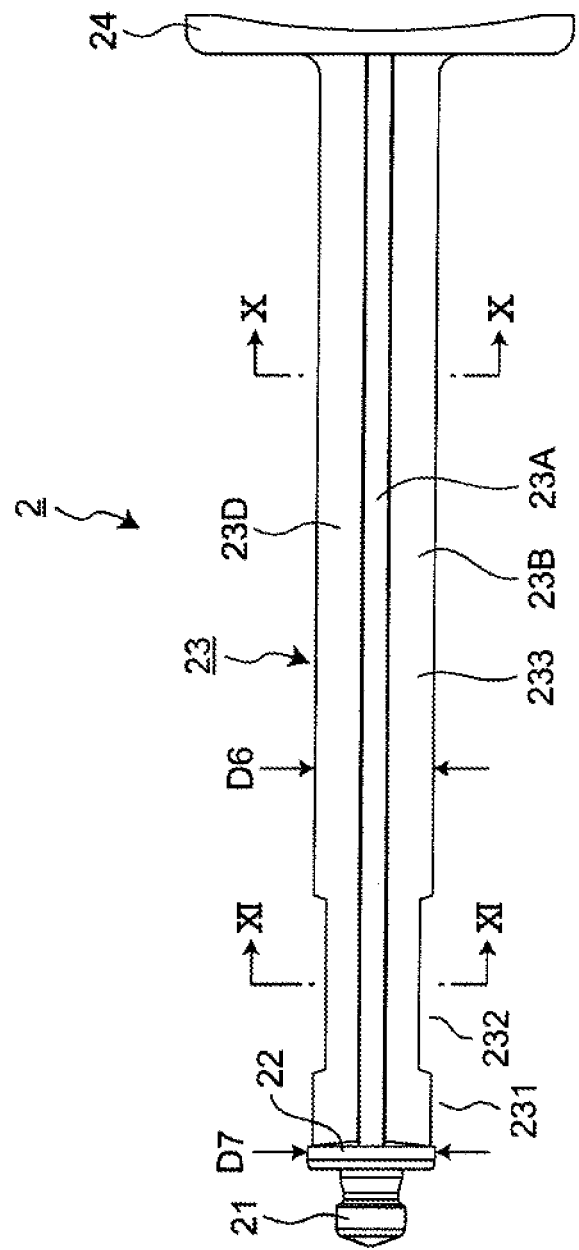
FIG. 8 is a plan view of a plunger rod.
Figure 9:
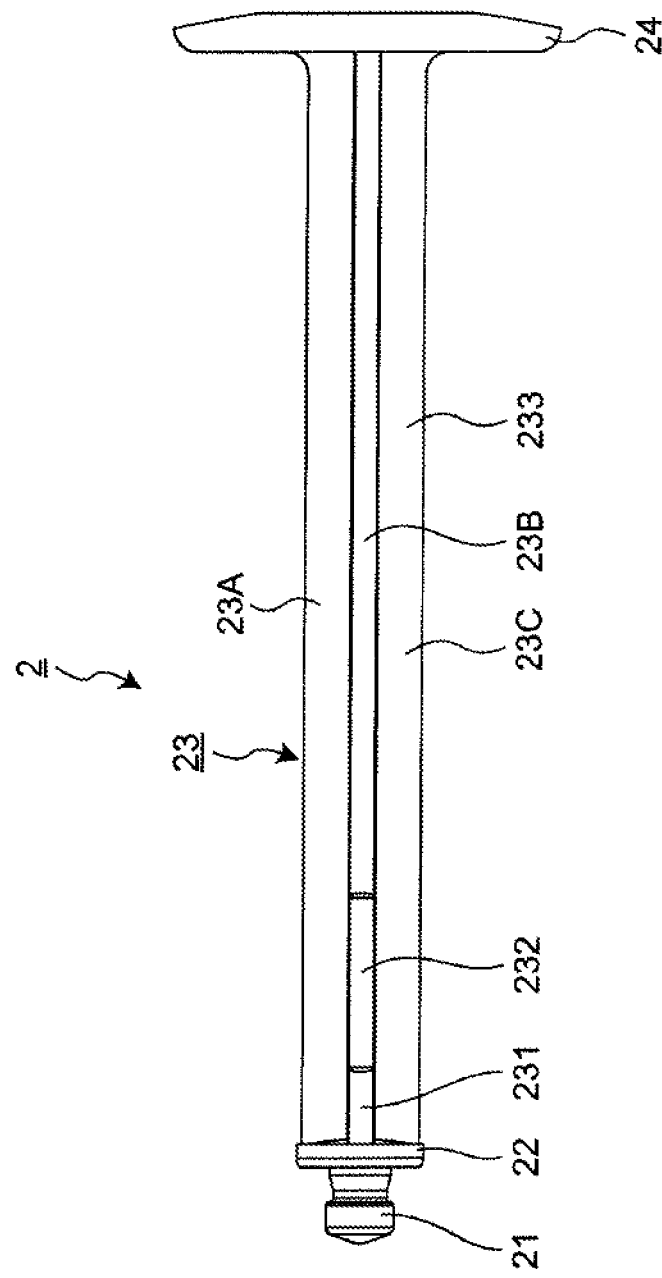
FIG. 9 is a side view of a plunger rod.
Figure 10:
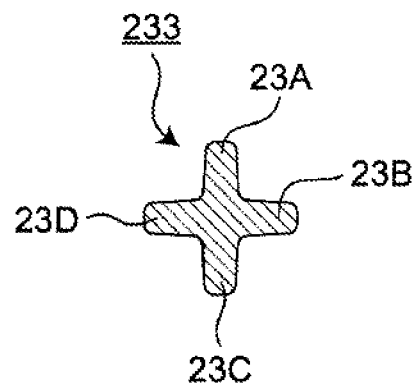
FIG. 10 is a cross-sectional view taken along the line X-X of FIG. 8.
Figure 11:
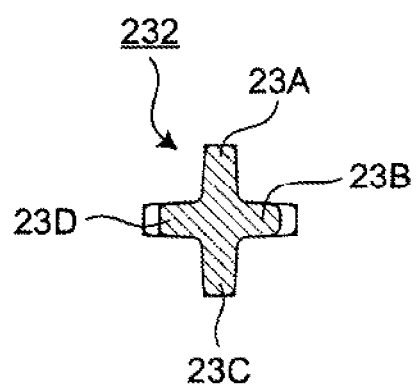
FIG. 11 is a cross-sectional view taken along the line XI-XI of FIG. 8.

FIG. 7 is a rear perspective view of the plunger rod 2. FIG. 8 is a plan view of the plunger rod 2. FIG. 9 is a side view of the plunger rod 2. FIG. 10 is a cross-sectional view taken along the line X-X of FIG. 8. FIG. 11 is a cross-sectional view taken along the line XI-XI of FIG. 8. The plunger rod 2 has, from the tip, a mounting portion 21 for the gasket 3, a flange 22 that supports the mounted gasket 3 from the rear side, a rod portion 23 having a cross-shaped cross section, and a pushing portion 24. The mounting portion 21 has a fitting form, but may have a screw form. The rod portion 23 has, from the tip, a mounting portion 231 for the stopper 4, a fitting portion (small diameter portion) 232 for the stopper 4, and a rod main body 233. As illustrated in FIG. 5, an axial dimension L1 of the fitting portion 232 is set to be the same as or slightly larger than an axial dimension L2 of the stopper 4.

The rod portion 23 includes four plates 23A, 23B, 23C, and 23D that vertically and horizontally protrude from the center. In the mounting portion 231 and the rod main body 233, protruding dimensions of the four plates 23A, 23B, 23C, and 23D are the same, as illustrated in FIG. 10. Meanwhile, in the fitting portion 232, protruding dimensions of the two plates 23B and 23D are set to be slightly smaller than the other plates 23A and 23C, as illustrated in FIG. 11.

Figure 12:
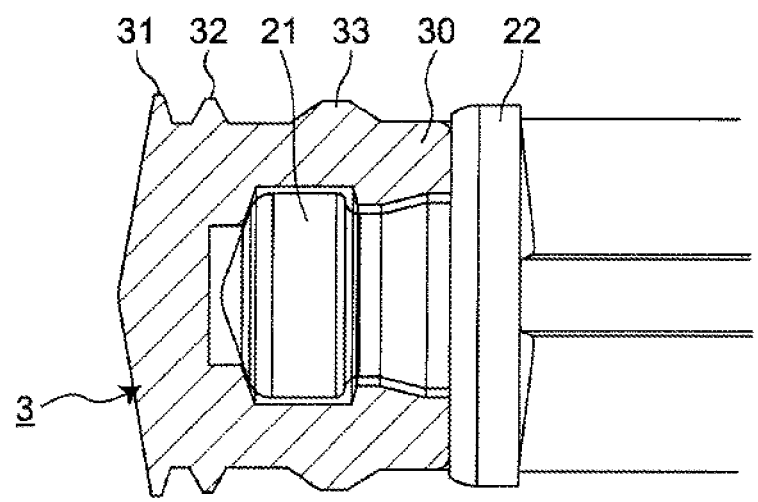
FIG. 12 is a partial cross-sectional view illustrating a gasket fixed by fitting to a mounting portion of a plunger rod.
Figure 13:
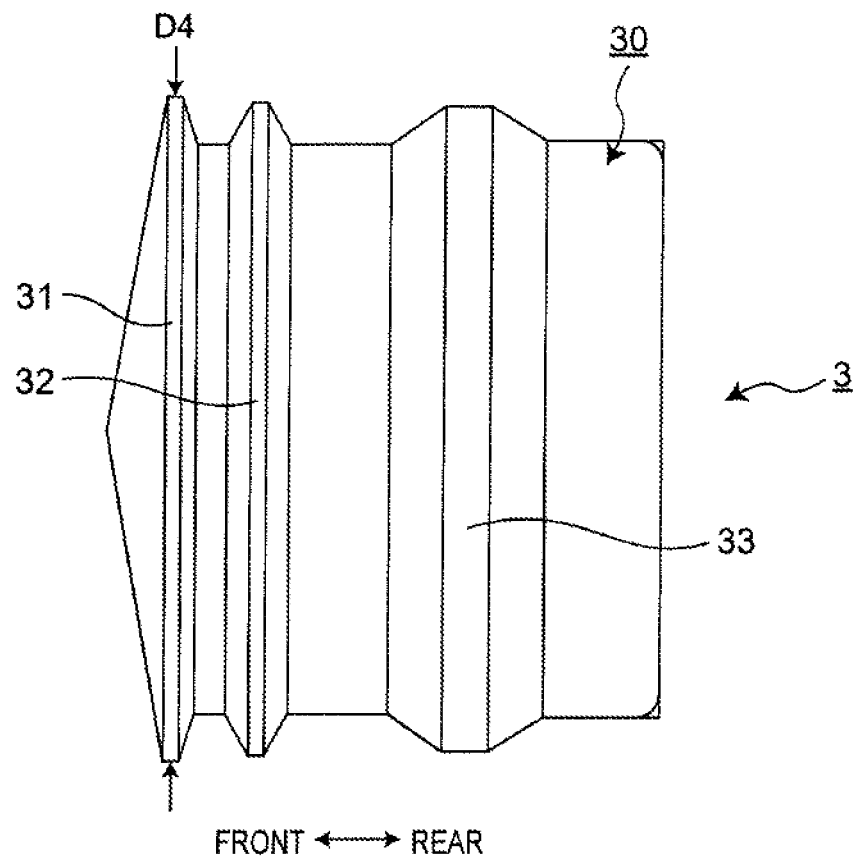
FIG. 13 is a plan view of a gasket.

As illustrated in FIG. 12, the gasket 3 is fixed by fitting to the mounting portion 21 of the plunger rod 2. Further, as illustrated in FIG. 13, the gasket 3 is a cylindrical body 30 having, on a periphery thereof, a first annular protruding portion 31, a second annular protruding portion 32, and a third annular protruding portion 33 in order from the front. The first annular protruding portion 31 has the outer diameter D4 and has a sealing function together with the second annular protruding portion 32 having an outer diameter smaller than that of the first annular protruding portion 31, and the third annular protruding portion 33 functions to stabilize sliding of the gasket 3. The gasket 3 may be a gasket of another form.

The gasket 3 is preferably made from polytetrafluoroethylene resin or tetrafluoroethylene/perfluoroalkyl vinyl ether copolymer resin. The gasket 3 may also be made from synthetic rubber. Synthetic rubber may be, for example, butyl rubber, SBR, BR, EPDM, fluorine rubber, NBR, silicone rubber, or the like. Further, the gasket 3 may have a configuration in which a fluororesin film is laminated on a surface of butyl rubber.

Figure 14:
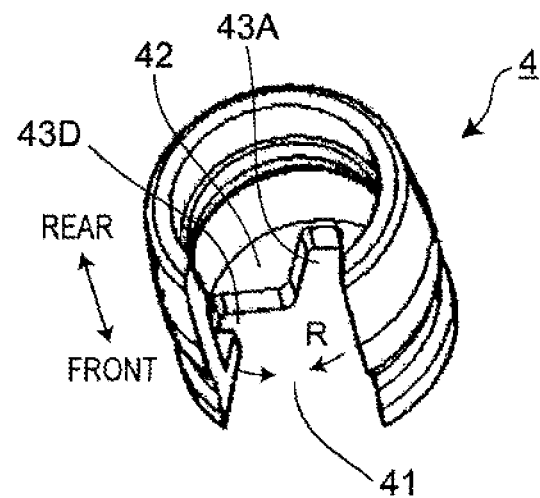
FIG. 14 is a rear lower perspective view of a stopper.
Figure 15:
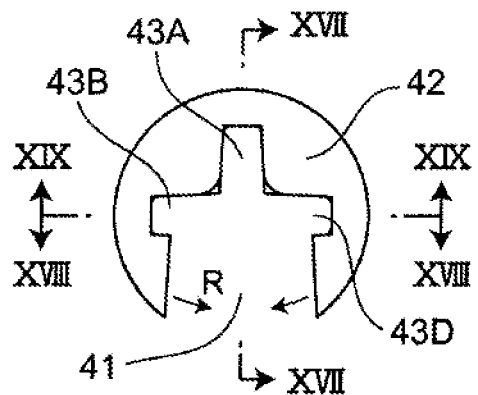
FIG. 15 is an XV arrow view of a stopper of FIG. 5.
Figure 16:
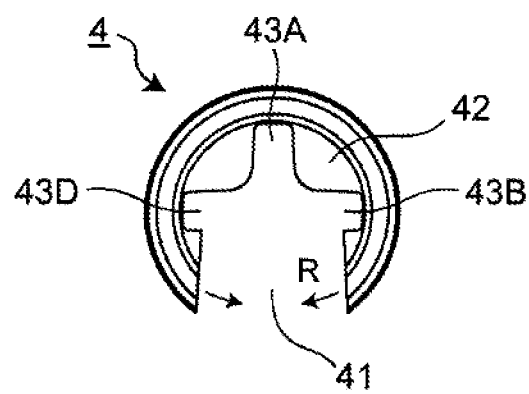
FIG. 16 is an XVI arrow view of the stopper of FIG. 5.
Figure 17:
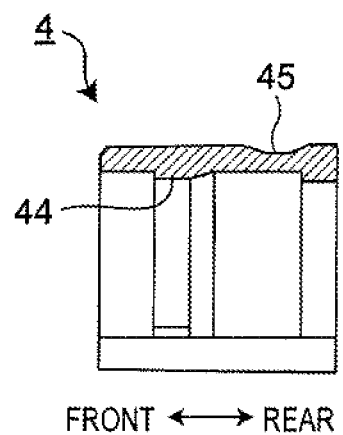
FIG. 17 is a cross-sectional view taken along the line XVII-XVII of FIG. 15.
Figure 18:
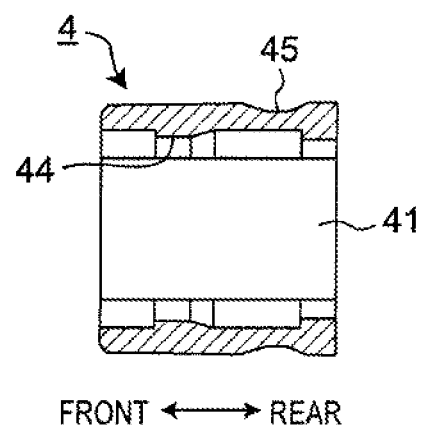
FIG. 18 is a cross-sectional view taken along the line XVIII-XVIII of FIG. 15.
Figure 19:
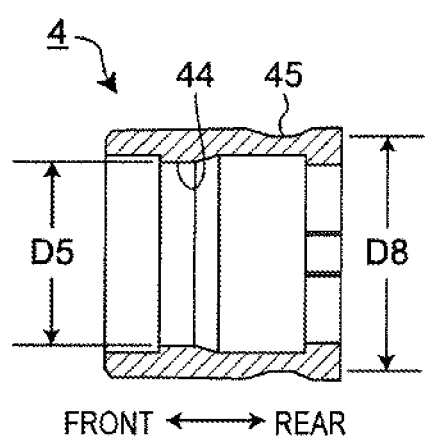
FIG. 19 is a cross-sectional view taken along the line XIX-XIX of FIG. 15.

FIG. 14 is a rear lower perspective view of the stopper 4. FIG. 15 is an XV arrow view of the stopper 4 of FIG. 5. FIG. 16 is an XVI arrow view of the stopper 4 of FIG. 5. FIG. 17 is a cross-sectional view taken along the line XVII-XVII of FIG. 15. FIG. 18 is a cross-sectional view taken along the line XVIII-XVIII of FIG. 15. FIG. 19 is a cross-sectional view taken along the line XIX-XIX of FIG. 15. The stopper 4 is a cylindrical body 40. The cylindrical body 40 has a split groove 41 extending in an axial direction. Therefore, the cylindrical body 40 can be bent in a direction of closing the split groove 41 as indicated by the arrow R of FIG. 14, and, as a result, the cylindrical body 40 is reduced in diameter. A front end of the cylindrical body 40 is open, and a rear end thereof is closed. That is, a closed portion 42 is provided at the rear end. Grooves 43A, 43B, and 43D through which the three plates 23A, 23B, and 23D of the rod portion 23 are inserted are formed in the closed portion 42. Note that the split groove 41 also serves as a groove through which the plate 23C is inserted. A protruding portion (third protruding portion) 44 is formed on an inner surface of a front portion of the cylindrical body 40. The protruding portion 44 is continuous in the circumferential direction except in the split groove 41. An inner diameter D5 (FIG. 19) of the protruding portion 44 is set to be the same as an outer diameter D6 of the rod main body 233, and is further set to be smaller than an outer diameter D7 of the flange 22 that supports the gasket 3. A recessed portion (first recessed portion) 45 that is continuous in the circumferential direction is formed on an outer surface of a rear portion of the cylindrical body 40. An outer diameter D8 (FIG. 19) of the recessed portion 45 is set to be the same as the inner diameter D3 of the protruding portion 131 of the syringe 1.

The injector 10 is assembled as follows.

Figure 20:
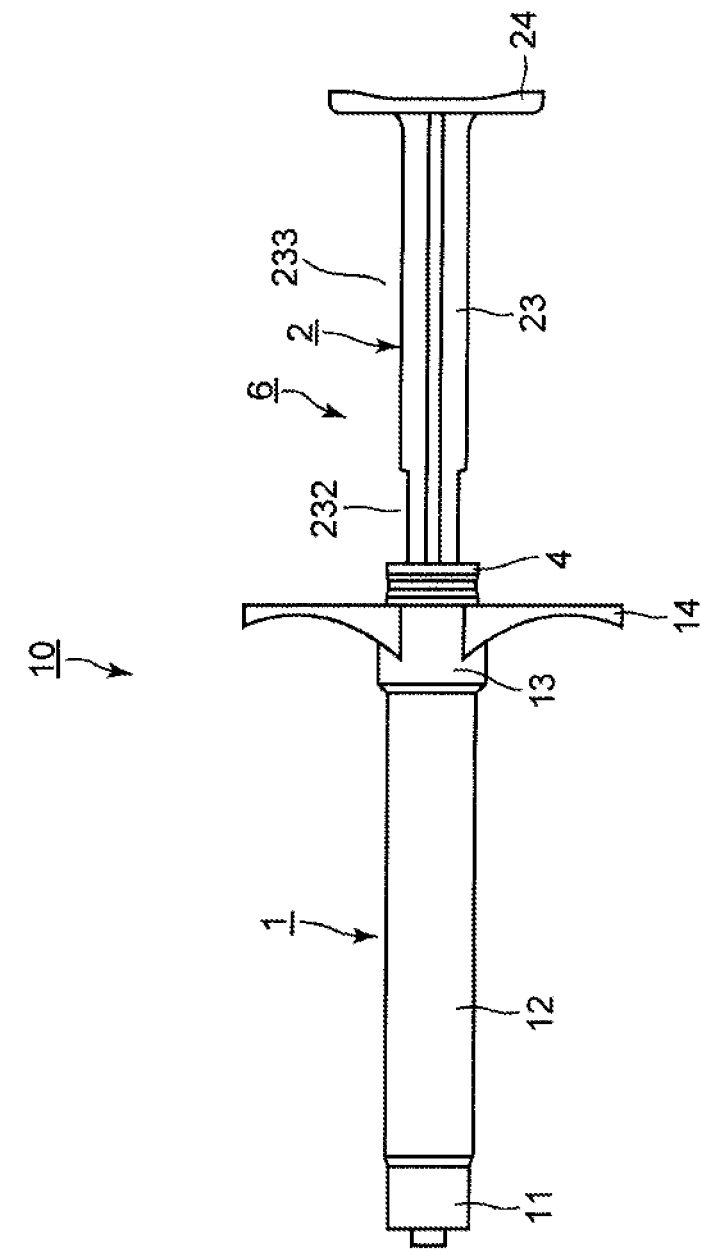
FIG. 20 is a plan view of an injector during assembly.
Figure 21:
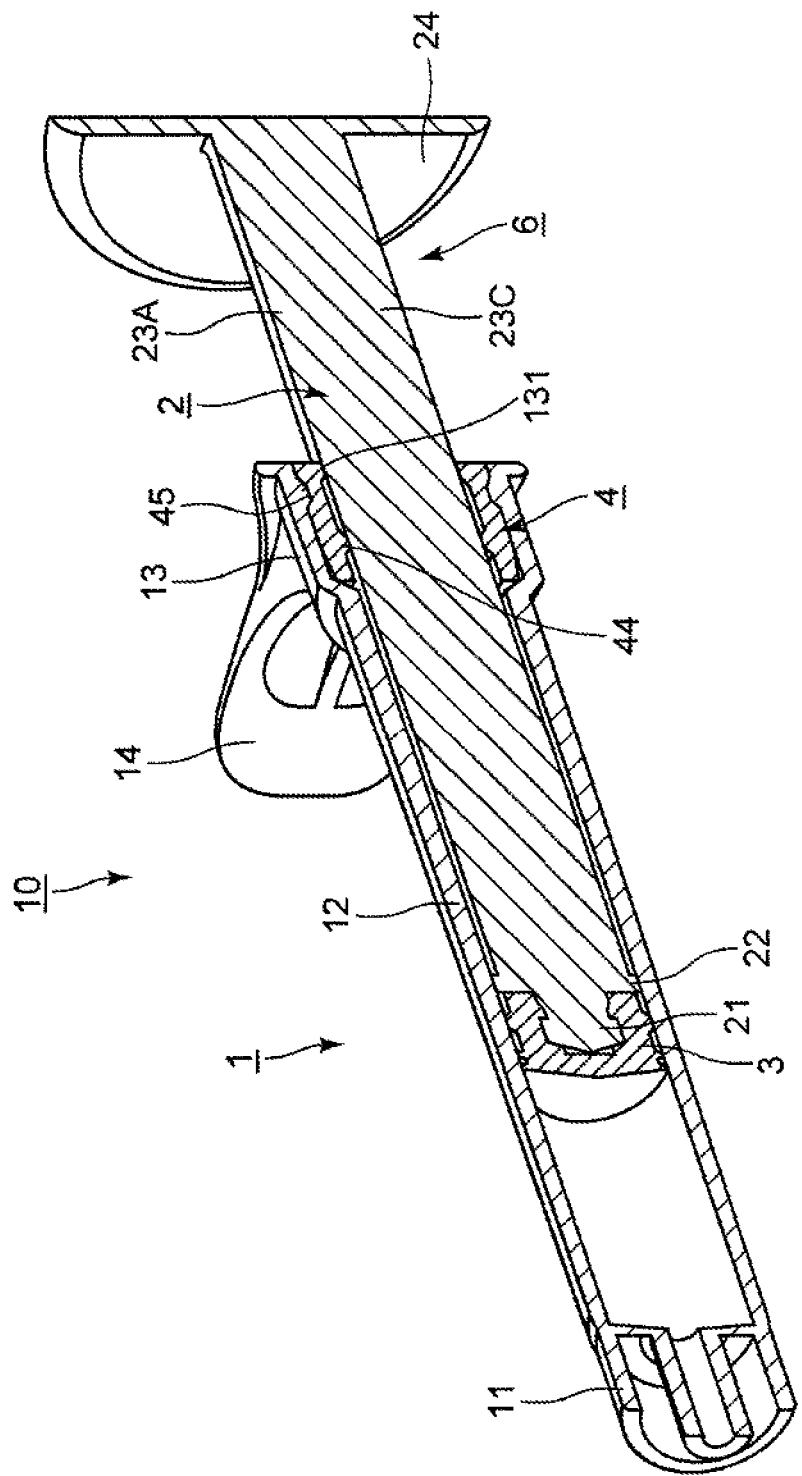
FIG. 21 is a perspective view illustrating a longitudinal section of an assembled injector, i.e., the injector of FIG. 1.

First, as illustrated in FIG. 4, in the plunger rod 2, the gasket 3 is mounted on the mounting portion 21 provided at the tip, and the stopper 4 is fitted into the fitting portion 232 of the rod portion 23. At this time, the stopper 4 is mounted on the fitting portion 232 so that the three plates 23A, 23B, and 23D are inserted into the grooves 43A, 43B, and 43D, respectively, while the closed portion 42 is facing rearward. Next, as illustrated in FIG. 20, the gasket 3 provided at the tip of the plunger 2 is inserted into the syringe 1 from the rear end of the syringe 1, and is fitted into the main body 12. Then, the stopper 4 externally fitted onto the fitting portion 232 is pushed into the mounting portion 231, i.e., into the rear end portion 13 of the syringe 1 while being reduced in diameter. The stopper 4 pushed into the rear end portion 13 is increased in diameter, and the protruding portion 131 of the rear end portion 13 of the syringe 1 is fitted into the recessed portion 45. Thus, the stopper 4 is fixed in the rear end portion 13 of the syringe 1 so as not to be movable in the axial direction. FIG. 21 is a perspective view illustrating a longitudinal section of the assembled injector 10, i.e., the injector 10 of FIG. 1.

The injector 10 having the above configuration has the following effects.

(1) The stopper 4 is reduced in diameter at the fitting portion 232 of the rod portion 23, and therefore the stopper 4 can be inserted into the rear end portion 13 of the syringe 1 and can further be fixed in the rear end portion 13 so as not to be movable in the axial direction. The inner diameter D5 of the protruding portion 44 is set to be smaller than the outer diameter D7 of the flange 22 that supports the gasket 3. Therefore, when the plunger 2 is pulled rearward, the flange 22 collides with the protruding portion 44 of the stopper 4. Thus, the plunger 2 cannot be further pulled rearward. That is, it is possible to prevent the plunger 2 from being pulled rearward to a degree to which the gasket 3 falls off from the syringe 1. Therefore, it is possible to achieve falling-off prevention of the gasket 3 with a simple configuration. This gasket falling-off prevention is achieved by the stopper 4, the fitting portion 232 of the rod portion 23, and the protruding portion 44 at the rear end portion 13 of the syringe 1.

(2) When the stopper 4 is inserted into the rear end portion 13 of the syringe 1, the stopper 4 is reduced in diameter at the fitting portion 232 of the rod portion 23, and thus the stopper 4 can be easily inserted into the rear end portion 13 of the syringe 1.

(3) The protruding portion 131 of the rear end portion 13 of the syringe 1 is continuous in the circumferential direction, and the recessed portion 45 of the stopper 4 is continuous in the circumferential direction except in the split groove 41, and thus the protruding portion 131 can be firmly fitted into the recessed portion 45. Therefore, the stopper 4 can be firmly fixed in the rear end portion 13 of the syringe 1 so as not to be movable in the axial direction.

(4) The inner diameter D3 of the protruding portion 131 of the rear end portion 13 of the syringe 1 is set to be the same as or slightly larger than the outer diameter D4 of the gasket 3, and thus it is possible to prevent a peripheral surface of the gasket 3 from being damaged by the protruding portion 131 when the gasket 3 is inserted into the syringe 1.

(5) The rod portion 23 of the plunger rod 2 is supported by the grooves 43A, 43B, and 43D of the closed portion 42 of the stopper 4 and the protruding portion 44 of the stopper 4, and thus the rod portion 23 is stable in the syringe 1, without being bent. Therefore, airtightness and liquid tightness of the gasket 3 are not impaired.

(6) The rod portion 23 of the plunger rod 2 can move back and forth along the grooves 43A, 43B, and 43D of the closed portion 42 of the stopper 4, and thus stable movement can be achieved.

Figure 22:
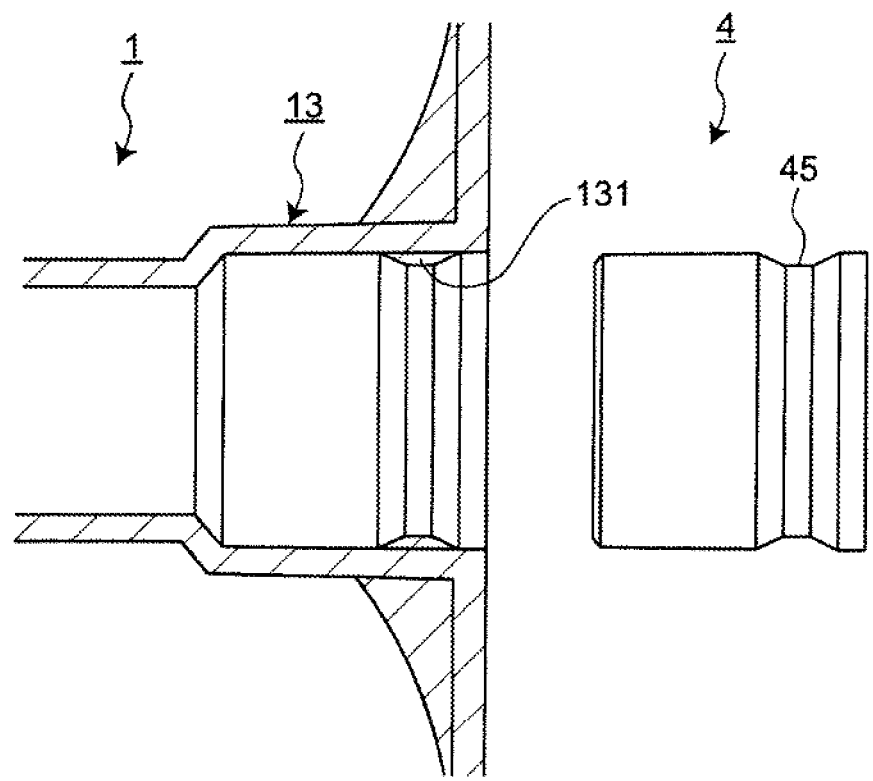
FIG. 22 is a partially enlarged cross-sectional view illustrating a fixing structure of a stopper.
Figure 23:
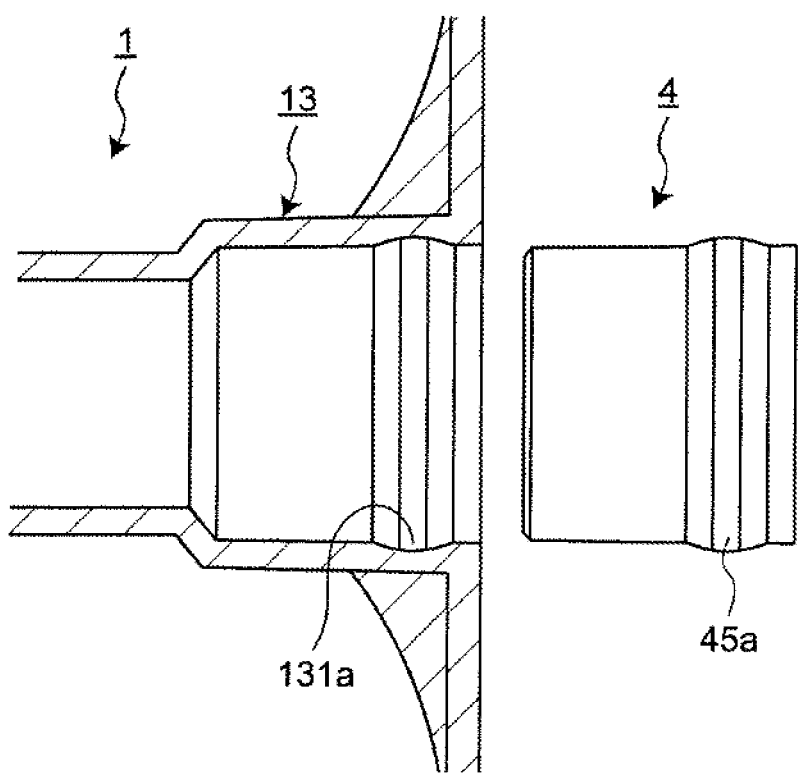
FIG. 23 is a partially enlarged cross-sectional view of a modification example.

Modification Example (1) In the above embodiment, as illustrated in FIG. 22, the protruding portion 131 of the syringe 1 is fitted into the recessed portion 45 of the stopper 4 in order to fix the stopper 4 in the rear end portion 13 of the syringe 1 so that the stopper 4 is not movable in the axial direction. However, as illustrated in FIG. 23, the protruding portion 45a of the stopper 4 may be fitted into a recessed portion 131a of the syringe 1.

INDUSTRIAL APPLICABILITY

The present invention can achieve gasket falling-off prevention with a simple structure and therefore has a high industrial utility value.

DESCRIPTION OF REFERENCE NUMERALS

1: Syringe
13: Rear end portion
131: (Second) protruding portion
2: Plunger rod
22: Flange
23: Rod portion
232: Fitting portion (small diameter portion)
3: Gasket
4: Stopper
41: Split groove
42: Closed portion
44: (Third) protruding portion
45: (First) recessed portion
6: Piston
10: Injector

The invention claimed is:

1. A gasket falling-off prevention mechanism that is provided in an injector and prevents a gasket provided at a tip of a piston from falling off through a rear end opening of a syringe, comprising a stopper being adapted to be fixed in a rear end portion of the syringe, wherein
the stopper is a cylindrical body having a split groove, is externally fitted onto a small diameter portion of a rod portion of a plunger rod of the piston before fixing, is deformed in a direction of closing the split groove at the small diameter portion when being fixed so as to have a diameter smaller than an inner diameter of the rear end portion of the syringe and be insertable into the rear end portion, and, after insertion, is increased in diameter and is fixed in the rear end portion so as not to be movable in an axial direction by fitting a first recessed portion or first protruding portion on a periphery into a second protruding portion or second recessed portion on an inner surface of the rear end portion of the syringe,
the stopper has a third protruding portion having an inner diameter smaller than an outer diameter of a gasket support flange of the rod portion in a fixed state,
the inner diameter of the rear end portion of the syringe is larger than an inner diameter of a main body of the syringe, and
the second protruding portion has an inner diameter equal to or larger than an outer diameter of the gasket.

2. The gasket falling-off prevention mechanism according to claim 1, wherein
the second protruding portion is continuously provided in a circumferential direction, and
the first recessed portion is continuously provided in the circumferential direction except in the split groove.

3. The gasket falling-off prevention mechanism according to claim 2, wherein
the rod portion of the plunger rod has a cross-shaped cross section,
the cylindrical body has an open front end and a closed rear end, and
a groove through which the rod portion having the cross-shaped cross section is inserted is provided in a closed portion of the cylindrical body, the closed portion being provided on a side opposite a side of the syringe.

4. The gasket falling-off prevention mechanism according to claim 1, wherein
the rod portion of the plunger rod has a cross-shaped cross section,
the cylindrical body has an open front end and a closed rear end, and
a groove through which the rod portion having the cross-shaped cross section is inserted is provided in a closed portion of the cylindrical body, the closed portion being provided on a side opposite a side of the syringe.

5. A gasket falling-off prevention mechanism that is provided in an injector and prevents a gasket provided at a tip of a piston from falling off through a rear end opening of a syringe, comprising a stopper being adapted to be fixed in a rear end portion of the syringe, wherein the stopper is a cylindrical body having a split groove, is externally fitted onto a small diameter portion of a rod portion of a plunger rod of the piston before fixing, is deformed in a direction of closing the split groove at the small diameter portion when being fixed so as to have a diameter smaller than an inner diameter of the rear end portion of the syringe and be insertable into the rear end portion, and, after insertion, is increased in diameter and is fixed in the rear end portion so as not to be movable in an axial direction by fitting a first recessed portion or first protruding portion on a periphery into a second protruding portion or second recessed portion on an inner surface of the rear end portion of the syringe, the stopper has a third protruding portion having an inner diameter smaller than an outer diameter of a gasket support flange of the rod portion in a fixed state, the second protruding portion is continuously provided in a circumferential direction, and the first recessed portion is continuously provided in the circumferential direction except in the split groove.

6. The gasket falling-off prevention mechanism according to claim 5, wherein the rod portion of the plunger rod has a cross-shaped cross section, the cylindrical body has an open front end and a closed rear end, and a groove through which the rod portion having the cross-shaped cross section is inserted is provided in a closed portion of the cylindrical body, the closed portion being provided on a side opposite a side of the syringe.

* * * * *